United States Patent [19]

Dusza et al.

[11] Patent Number: 4,626,538
[45] Date of Patent: * Dec. 2, 1986

[54] [7-(3-DISUBSTITUTED AMINO)PHENYL]PYRAZOLO[1,5-A]PYRIMIDINES

[75] Inventors: John P. Dusza, Nanuet, N.Y.; Andrew S. Tomcufcik, Old Tappan, N.J.; Jay D. Albright, Nanuet, N.Y.

[73] Assignee: American Cyanamid Company, Stamford, Conn.

[*] Notice: The portion of the term of this patent subsequent to Jun. 3, 2002 has been disclaimed.

[21] Appl. No.: 732,986

[22] Filed: May 13, 1985

Related U.S. Application Data

[63] Continuation-in-part of Ser. No. 612,812, May 24, 1984, Pat. No. 4,521,422, which is a continuation-in-part of Ser. No. 506,966, Jun. 23, 1983, abandoned.

[51] Int. Cl.$^4$ .................. A61K 31/505; C07D 471/04
[52] U.S. Cl. .................... 514/258; 514/906; 544/281
[58] Field of Search ............. 544/281; 514/258

[56] References Cited

U.S. PATENT DOCUMENTS

| | | | |
|---|---|---|---|
| 4,178,449 | 12/1979 | Dusza et al. | 544/281 |
| 4,236,005 | 11/1980 | Dusza et al. | 544/281 |
| 4,281,000 | 7/1981 | Dusza et al. | 544/281 |
| 4,521,422 | 6/1985 | Dusza et al. | 544/281 |
| 4,576,943 | 3/1986 | Tomcufcik et al. | 544/281 |

Primary Examiner—Donald G. Daus
Assistant Examiner—Stephen M. Kapner
Attorney, Agent, or Firm—Susan H. Rauch

[57] ABSTRACT

Novel [7-(3-disubstituted amino)phenyl]pyrazolo[1,5-a]pyrimidines useful as anxiolytic, antiepileptic and sedative-hypnotic agents as well as skeletal muscle relaxants, methods of using these compounds, compositions of matter containing them and processes for their production.

15 Claims, No Drawings ately at reflux giving an N-[3-[3-(dimethylamino)-1-oxo-2-propenyl[phenyl]alkanamide, which is then reacted
[7-(3-DISUBSTITUTED AMINO)PHENYL]PYRAZOLO[1,5-A]PYRIMIDINES

CROSS REFERENCE TO RELATED APPLICATIONS

This application is a continuation-in-part of our copending application, U.S. application Ser. No. 612,812, filed May 24, 1984, now U.S. Pat. No. 4,521,422, which is a continuation-in-part of U.S. application Ser. No. 506,966, filed June 23, 1983, now abandoned.

SUMMARY OF THE INVENTION

This invention relates to new organic compounds which are [7-(3-disubstituted amino)phenyl]-pyrazolo[1,5-a]pyrimidines, which are useful as anxiolytic and antiepileptic agents as well as sedative-hypnotic agents and skeletal muscle relaxants. This invention also relates to the methods of using the novel compounds, to compositions of matter containing them as the active ingredient and to processes for their production.

DETAILED DESCRIPTION OF THE INVENTION

The novel compounds of this invention are represented by the following structural formula:

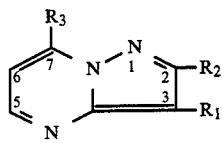

wherein $R_1$ is selected from the group consisting of: hydrogen, halogen, cyano and

$R_2$ is selected from the group consisting of hydrogen and alkyl($C_1$-$C_3$); $R_3$ is

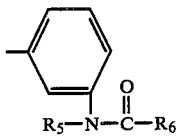

$R_4$ is selected from the group consisting of hydrogen, alkyl($C_1$-$C_6$) and alkoxy($C_1$-$C_6$); $R_5$ is selected from the group consisting of hydrogen, alkyl($C_1$-$C_6$), alkenyl(-$C_2$-$C_6$), —$CH_2C\equiv CH$, cycloalkyl($C_3$-$C_6$)methyl, —$CH_2OCH_3$ and —$CH_2CH_2OCH_3$; and $R_6$ is selected from the group consisting of alkyl($C_1$-$C_6$), cycloalkyl(-$C_3$-$C_6$), —O—alkyl($C_1$-$C_6$), —NH—alkyl($C_1$-$C_3$), —N—dialkyl($C_1$-$C_3$), —($CH_2$)$_n$—O—alkyl($C_1$-$C_3$), —($CH_2$)$_n$—NH-alkyl($C_1$—$C_3$) and —($CH_2$)$_n$—N—dialkyl($C_1$-$C_3$), where n is an integer 1 to 3 inclusive.

The most preferred compounds of this invention are the compounds of the above formula wherein $R_1$ is cyano or

$R_2$ is hydrogen; $R_4$ is alkyl($C_1$-$C_6$); $R_5$ is alkyl($C_1$-$C_6$), alkenyl($C_2$-$C_6$) or —$CH_2\equiv CH$; and $R_6$ is alkyl($C_1$-$C_6$), cycloalkyl($C_3$-$C_6$) or —O —alkyl($C_1$-$C_6$).

The instant invention is additionally concerned with the methods which employ the above-described compounds in mammals to treat anxiety or epilepsy and to induce a sedative-hypnotic effect or relax skeletal muscles, with compositions of matter containing the above-described compounds and with processes for producing the compounds.

The novel compounds of this invention may be readily prepared as set forth in the following reaction scheme:

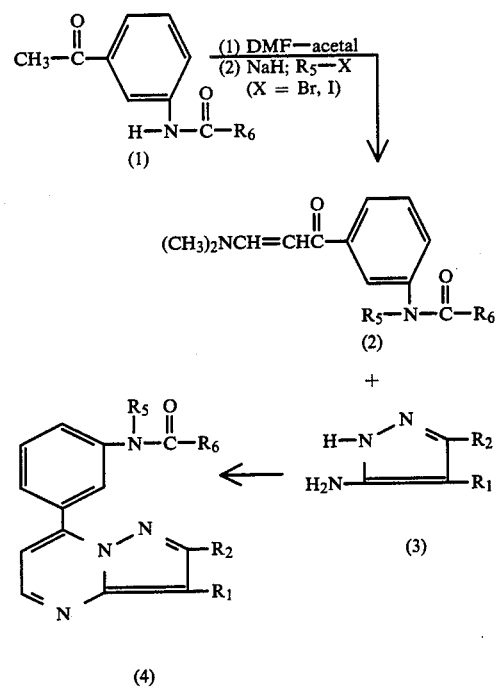

In accordance with the above reaction scheme a 1-acetylphenyl-3-amide (1), where $R_6$ is as described above is reacted with dimethylformamide dimethylacetal at reflux giving an N-[3-[3-(dimethylamino)-1-oxo-2-propenyl[phenyl]alkanamide, which is then reacted with sodium hydride, and the anion generated is reacted with an alkyl halide, where $R_5$ is as described, above giving the N-[3-[3-(dimethylamino)-1-oxo-2-propenyl]-phenyl]-N-alkylalkanamide (2). This compound is than reacted with a 3-aminopyrazole (3), where $R_1$ and $R_2$ are as described above, in glacial acetic acid at reflux, giving the product (4).

Alternatively, N-[3-[3-(dialkylamino)-1-oxo-2-propenyl]phenyl]alkanamide (5) is reacted with a 3-aminopyrazole (3) to give intermediates (6) which are reacted with a base such as sodium hydride, sodium alkoxide and the like and an $R_5$-halide to give the products (4).

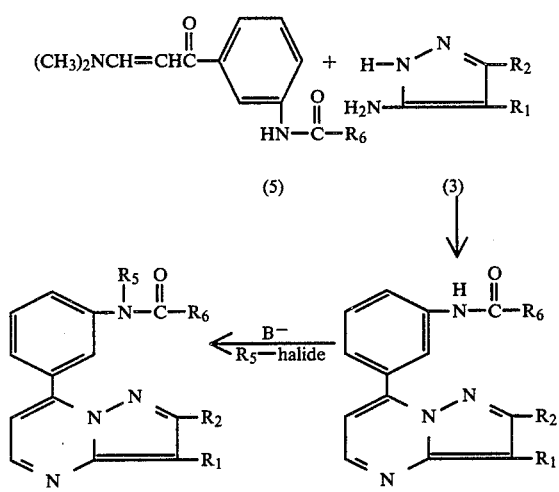

Details of the preparative scheme are fully apparent from the U.S. Pat. No. 4,521,422, which is hereby incorporated by reference.

The performance of the novel compounds of the present invention in standard tests with laboratory animals which are known to correlate well with relief of anxiety in man indicates that they possess central nervous system activity at nontoxic doses and thus are useful as anxiolytic agents. Furthermore, these compounds have been shown by biological data to be useful as antiepileptic agents, particularly in the treatment of grand mal epilepsy seizures, and as sedative-hypnotic and skeletal muscle relaxant agents.

The anti-anxiety and anticonvulsant properties of the novel compounds of the present invention have been established in a test which indicates anxiolytic and antiepileptic activity by the measure of protection they provide from convulsions resulting from the administration of pentylenetetrazole. Single or graded dose levels of the test compounds were administered orally or intraperitoneally in a 2% starch vehicle, containing 0.5% v/v polyethylene glycol and one drop of Polysorbate 80 to groups of at least 4 rats. At 30 or 60 minutes, the rats were treated intravenously with pentylenetetrazole at a dose of 23 mg/kg of body weight. This dose is estimated to cause clonic seizures in 99% of unprotected rats. It has been reported [R. T. Hill and D. H. Tedeschi, "Animal Testing and Screening Procedures in Evaluating Psychotropic Drugs" in "An Introduction to Psychopharmacology", Eds. R. R. Rech and K. E. Moore, Raven Press, New York, p. 237-288 (1971)] that there is a high degree of correlation between the ability of compounds to inhibit the seizure-inducing effect of pentylenetetrazole in rats and the effectiveness of those compounds as anxiolytic and anticonvulsive agents in higher warm-blooded animals. The results of this test on representative compounds of the present invention are shown in Table I.

TABLE I

| Protection Against Clonic Seizures Caused by Pentylenetetrazole in Rats | | |
|---|---|---|
| Compound | Dose (mg/kg) | % of Rats Protected |
| N—[3-(3-cyanopyrazolo[1,5-a]pyrimidin-7-yl)phenyl]-N—ethylpropanamide | 25.0 | 100 |
| N—[3-(3-cyanopyrazolo[1,5-a]pyrimidin-7-yl)phenyl]-N—ethylacetamide | 25.0 | 100 |
| N—[3-(3-chloropyrazolo[1,5-a]pyrimidin-7-yl)phenyl]-N—ethylacetamide | 25.0 | 100 |
| N—[3-(3-cyanopyrazolo[1,5-a]pyrimidin-7-yl)phenyl]-N—propylacetamide | 6.25 | 100 |
| [3-(3-cyanopyrazolo[1,5-a]pyrimidin-7-yl)phenyl]methylcarbamic acid, methyl ester | 3.1 | 25 |
| [3-(3-cyanopyrazolo[1,5-a]pyrimidin-7-yl)phenyl]ethylcarbamic acid, methyl ester | 12.6 | 75 |
| N—butyl-N—[3-(3-cyanopyrazolo[1,5-a]pyrimidin-7-yl)phenyl]acetamide | 25.0 | 50 |
| [3-(3-cyanopyrazolo[1,5-a]pyrimidin-7-yl)phenyl]ethylcarbamic acid, ethyl ester | 25.0 | 25 |
| [3-(3-chloropyrazolo[1,5-a]pyrimidin-7-yl)phenyl]ethylcarbamic acid, ethyl ester | 25.0 | 25 |
| N—[3-(3-cyanopyrazolo[1,5-a]pyrimidin-7-yl)phenyl]-N—2-propenylacetamide | 25.0 | 100 |
| N—[3-(3-cyanopyrazolo[1,5-a]pyrimidin-7-yl)phenyl]-N—2-propynylacetamide | 6.25 | 100 |
| N—[3-(3-cyanopyrazolo[1,5-a]pyrimidin-7-yl)phenyl]-N—methylcyclobutanecarboxamide | 25.0 | 50 |
| N—[3-(3-cyanopyrazolo[1,5-a]pyrimidin-7-yl)phenyl]-N—methylcyclopropanecarboxamide | 25.0 | 75 |
| N—[3-(3-cyanopyrazolo[1,5-a]pyrimidin-7-yl)phenyl]-N—methylacetamide | 25.0 | 75 |
| N—[3-(3-cyanopyrazolo[1,5-a]pyrimidin-7-yl)phenyl]-N—methylacetamide | 12.5 | 50 |
| 7-[3-(acetylmethylamino)phenyl]pyrazolo[1,5-a]pyrimidine-3-carboxylic acid, ethyl ester | 25.0 | 100 |
| N—[3-(3-cyanopyrazolo[1,5-a]pyrimidin-7-yl)phenyl]-N—methylpropanamide | 12.5 | 50 |
| N—[3-(3-cyano-2-methylpyrazolo[1,5-a]pyrimidin-7-yl)phenyl]-N—methylpropanamide | 25.0 | 100 |

Another test which has been used to assess antianxiety effects is a nonconditioned passive avoidance procedure described by J. R. Vogel, B. Beer and D. E. Clody, "A Simple and Reliable Conflict Procedure for Testing Anti-Anxiety Agents", Psychopharmacologia, 21, 1–7 (1971). A conflict situation is induced in rats by a modification of this method.

Groups of 6 native, Wistar strain rats, weighing 200-240 g each were deprived of water for 48 hours and food for 24 hours. The test compounds were administered in single or graded, oral or intraperitoneal doses, suspended in a 2% starch vehicle containing 0.5% v/v polyethylene glycol and one drop of polysorbate 80. Control animals received the vehicle alone. At 30 to 60 minutes each rat was placed in an individual plexiglass chamber. Water was available ad libitum from a tap located in the rear of the chamber. A 0.7 milliampere DC shocking current was established between the stainless steel grid floor and the tap. After 20 licks of non-shocked drinking, a shock was delivered for 2 seconds and then further shocks were delivered on a ratio of one shock for 2 seconds for every 20 licks. This was continued for a total of 3 minutes. The number of shocks taken by each rat during the 3 minute interval was recorded and compared to a control group. The test compounds are considered active if the number of shocks received by the test group is significantly higher than the control group by the Mann-Witney U test. Results of this test on representative compounds of this invention appear in Table II.

TABLE II

Noncondition Passive Avoidance Test in Rats

| Compound | Dose (mg/kg) | Result |
|---|---|---|
| N—3-(3-cyanopyrazolo[1,5-a]pyrimidin-7-yl)phenyl]-N—ethylpropanamide | 0.4 | Active |
| N—3-(3-cyanopyrazolo[1,5-a]pyrimidin-7-yl)phenyl]N—ethylacetamide | 0.8 | Active |
| N—ethyl-N—(3-pyrazolo[1,5-a]pyrimidin-7-ylphenyl)acetamide | 25.0 | Active |
| N—[3-(3-chloropyrazolo[1,5-a]pyrimidin-7-yl)phenyl]-N—ethylacetamide | 3.1 | Active |
| N—[3-(3-cyanopyrazolo[1,5-a]pyrimidin-7-yl)phenyl]-N—propylacetamide | 1.5 | Active |
| [3-(3-cyanopyrazolo[1,5-a]pyrimidin-7-yl)phenyl]methylcarbamic acid, methyl ester | 3.1 | Active |
| [3-(3-cyanopyrazolo[1,5-a]pyrimidin-7-yl)phenyl]ethylcarbamic acid, methyl ester | 12.5 | Active |
| [3-(3-chloropyrazolo[1,5-a]pyrimidin-7-yl)phenyl]ethylcarbamic acid, ethyl ester | 25.0 | Active |
| N—[3-(3-cyanopyrazolo[1,5-a]pyrimidin-7-yl)phenyl]-N—2-propenylacetamide | 3.1 | Active |
| N—[3-(3-cyanopyrazolo[1,5-a]pyrimidin-7-yl)phenyl]-N—2-propynylacetamide | 1.5 | Active |
| N—[3-(3-cyanopyrazolo[1,5-a]pyrimidin-7-yl)phenyl]-N—methylpropaneamide | 6.2 | Active |
| N—[3-(3-cyano-2-methylpyrazolo[1,5-a]-pyrimidin-7-yl)phenyl]-N—methylpropanamide | 25.0 | Active |
| 7-[3-(acetylmethylamino)phenyl]pyrazolo[1,5-a]pyrimidine-3-carboxylic acid, ethyl ester | 25.0 | Active |
| N—[3-(3-cyanopyrazolo[1,5-a]pyrimidin-7-yl)phenyl]-N—methylacetamide | 1.5 | Active |
| N—[3-(3-chloropyrazolo[1,5-a]pyrimidin-7-yl)phenyl]-N—methylacetamide | 3.1 | Active |
| N—[3-(3-cyanopyrazolo[1,5-a]pyrimidin-7-yl)phenyl]-N—methylcyclobutanecarboxamide | 25.0 | Active |

Another test utilized for the determination of anxiolytic activity is the measurement of the ability of test compounds to inhibit the binding of tritiated benzodiazepines to brain-specific receptors of warm-blooded animals. A modification of the method described by R. F. Squires, et al., Nature, 266, No. 21, p. 732 (April 1977) and H. Mohler, et al., Science, 198, p. 849 (1977) was employed.

Male albino rats (Wistar strain, weighing 150–200 g each) were obtained from Royalhart Farms. $^3$H-Methyldiazepam (79.9 Ci/mmol) and $^3$H-methylflunitrazepam (84.3 Ci/mmol) were obtained from New England Nuclear. The test compounds were solubilized in either dimethylformamide, acetic acid, ethanol or hydrochloric acid.

Whole cortex of rats was homogenized gently in 20 volumes of ice-cold 0.32 M sucrose, centrifuged twice at 1000 g for 10 minutes and then recentrifuged at 30,000 g for 20 minutes to produce a crude $P_2$-synaptosomal fraction. The $P_2$-fraction was either: (1) resuspended in twice the original volume in hypotonic 50 mM Tris.HCl (pH 7.4), or (2) resuspended in one-half the original volume in hypotonic 10 mM Tris.HCl (pH 7.4) and then was frozen (−20° C.) until time of use. Frozen $P_2$ preparations were thawed and resuspended in four times the original homogenizing volume at time of assay.

The binding assay consisted of 300 μl of the $P_2$-fraction suspension (0.2–0.4 mg protein), 100 μl of test drug and 100 μl of $^3$H-diazepam (1.5 nM, final concentration) or $^3$H-flunitrazepam (1.0 nM, final concentration) which was added to 1.5 ml of 50 mM Tris.HCl (pH 7.4). Non-specific binding controls and total binding controls received 100 μl of diazepam (3 M, final concentration) and 100 μl of deionized water, respectively, in place of the test compound. Incubation for 30 minutes proceeded in ice and was terminated by filtration, under vacuum, through Whatman GF/C glass fiber filters. The filters were washed twice with 5 ml of ice-cold 50 mM Tris.HCl (pH 7.4) and placed in scintillation vials. After drying at 50°–60° C. for 30 minutes, 10 ml of Beckman Ready-Solv TM HP (a high performance premix scintillation cocktail, registered trademark of Beckman Instruments, Inc., Irvine, CA 92713) was added and the radioactivity determined in a scintillation counter.

Inhibition of binding was calculated by the difference between total binding and binding in the presence of test compound, divided by the total binding × 100.

The results of this test on representative compounds of the present invention are given in Table III.

TABLE III

Inhibition of the Binding of $^3$H—Benzodiazepine to Brain-Specific Receptors of Rats

| Compound | % Inhibition |
|---|---|
| N—[3-(3-cyanopyrazolo[1,5-a]pyrimidin-7-yl)phenyl]-N—ethylpropanamide | 83 |
| N—[3-(3-cyanopyrazolo[1,5-a]pyrimidin-7-yl)phenyl]-N—ethylacetamide | 79 |
| N—[3-(3-chloropyrazolo[1,5-a]pyrimidin-7-yl)phenyl]-N—ethylacetamide | 97 |
| N—[3-(3-cyanopyrazolo[1,5-a]pyrimidin-7-yl)phenyl]-N—propylacetamide | 64 |
| 7-[3-[ethyl(1-oxopropyl)amino]phenyl]pyrazolo[1,5-a]pyrimidine-3-carboxylic acid, ethyl ester | 100 |
| [3-(3-cyanopyrazolo[1,5-a]pyrimidin-7-yl)phenyl]methylcarbamic acid, methyl ester | 87 |
| 7-[3-[(methoxycarbonyl)methylamino]phenyl]-pyrazolo[1,5-a]pyrimidine-3-carboxylic acid, ethyl ester | 98 |
| [3-(3-cyanopyrazolo[1,5-a]pyrimidin-7-yl)-phenyl]ethylcarbamic acid, methyl ester | 55 |
| 7-[3-[ethyl(methoxycarbonyl)amino]phenyl]-pyrazolo[1,5-a]pyrimidine-3-carboxylic acid, ethyl ester | 99 |
| [3-(3-cyanopyrazolo[1,5-a]pyrimidin-7-yl)-phenyl]methylcarbamic acid, methyl ester | 41 |
| ethyl(3-pyrazolo[1,5-a]pyrimidin-7-yl-phenyl)carbamic acid, ethyl ester | 61 |
| [3-(3-cyanopyrazolo[1,5-a]pyrimidin-7-yl)-phenyl]ethylcarbamic acid, ethyl ester | 63 |
| [3-(3-chloropyrazolo[1,5-a]pyrimidin-7-yl)-phenyl]ethylcarbamic acid, ethyl ester | 78 |
| N—[3-(3-cyanopyrazolo[1,5-a]pyrimidin-7-yl)phenyl]-N—2-propenylacetamide | 78 |
| N—[3-(3-cyanopyrazolo[1,5-a]pyrimidin-7-yl)phenyl]-N—2-propynylacetamide | 91 |
| N—[3-(3-cyano-2-methylpyrazolo[1,5-a]pyrimidin-7-yl)phenyl]propanamide | 42 |
| N—[3-(3-cyanopyrazolo[1,5-a]pyrimidin-7-yl)phenyl]-N—methylpropanamide | 79 |
| N—[3-(3-cyano-2-methylpyrazolo[1,5-a]-pyrimidin-7-yl)phenyl]-N—methylpropanamide | 95 |
| N—methyl-N—(3-pyrazolo[1,5-a]pyrimidin-7-ylphenyl)acetamide | 54 |
| 7-[3-(acetylmethylamino)phenyl]pyrazolo-[1,5-a]pyrimidine-3-carboxylic acid, ethyl ester | 100 |
| N—[3-(3-cyanopyrazolo[1,5-a]pyrimidin-7-yl)phenyl]-N—methylacetamide | 73 |
| N—[3-(3-chloropyrazolo[1,5-a]pyrimidin-7-yl)phenyl]-N—methylacetamide | 71 |
| N—[3-(3-cyanopyrazolo[1,5-a]pyrimidin-7-yl)phenyl[-N—methylcyclobutanecarboxiamde | 81 |
| N—[3-(3-cyanopyrazolo[1,5-a]pyrimidin-7- | 83 |

TABLE III-continued

Inhibition of the Binding of $^3$H—Benzodiazepine to Brain-Specific Receptors of Rats

| Compound | % Inhibition |
|---|---|
| yl)phenyl]-N—methylcyclopropanecarboxamide | |
| 7-[3-[(cyclopropylcarbonyl)methylamino]-phenylpyrazolo[1,5-a]pyrimidine-3-carboxylic acid, ethyl ester | 95 |
| 7-[3-(acetylethylamino)phenyl]pyrazolo-[1,5-a]pyrimidine-3-carboxylic acid, ethyl ester | 97 |
| 7-[3-(acetylamino)phenyl]pyrazolo[1,5-a]-pyrimidine-3-carboxylic acid, ethyl ester | 85 |
| 7-[3-[(methoxycarbonyl)amino]phenyl]-pyrazolo[1,5-a]pyrimidine-3-carboxylic acid, ethyl ester | 76 |
| methyl(3-pyrazolo[1,5-a]pyrimidin-7-yl-phenyl)carbamic acid, methyl ester | 45 |
| 7-[3-(acetylpropylamino)phenyl]pyrazolo-[1,5-a]pyrimidine-3-carboxylic acid, ethyl ester | 97 |
| [3-(3-chloropyrazolo[1,5-a]pyrimidin-7-yl)phenyl]methylcarbamic acid, methyl ester | 92 |
| 7-[3-[(cyclobutylcarbonyl)amino]phenyl]-pyrazolo[1,5-a]pyrimidine-3-carboxylic acid, ethyl ester | 82 |

The novel compounds of this invention have also been shown to have skeletal muscle relaxant activity through the use of two tests. The first test measures the effect of representative compounds on the ability of rats to remain on an inclined screen. Groups of at least 6 rats were treated orally with graded doses of test compounds or vehicle and placed on a wire mesh screen (inclined at an angle of 60° from a horizontal level) 65 minutes later. The number of rats falling off the screen within 30 minutes was recorded. The ED$_{50}$ (dose necessary to cause 50% of the animals tested to fall off) was calculated according to the linear arcsine transformation method of Finney, D. J., "Statistical Methods in Biological Assay", 2nd Ed., Hafner, N.Y., 1964, p. 454. Compounds were dissolved or suspended in a 2% aqueous starch suspension containing 5% polyethylene glycol 400 and a drop of polysorbate 80, and administered in a constant volume of 5 ml/kg. The results of representative compounds of this invention appear in Table IV.

TABLE IV

Effect on Ability of Rats to Remain on an Inclined Screen

| Compound | ED$_{50}$ (mg/kg) |
|---|---|
| N—[3-(3-cyanopyrazolo[1,5-a]pyrimidin-7-yl)phenyl]-N—ethylpropanamide | 4.6 |
| N—[3-(3-cyanopyrazolo[1,5-a]pyrimidin-7-yl)phenyl]-N—ethylacetamide | 3.9 |

The second test to illustrate that the novel compounds of the present invention possess skeletal muscle relaxant properties shows the effect of representative compounds on the locomotor activity in rats. Groups of 6 rats were treated orally with vehicle (5 ml/kg) or graded doses of the test compounds. Sixty minutes later, individual rats were placed in Actophotometers and locomotor activity was measured for 5 minutes after a brief (30 sec.) habituation period. Motor activity counts (number of crossings of the photo cells) were recorded for each rat, and mean activity counts were calculated for each treatment group. The dose causing a 50% decrease in mean activity counts compared with the vehicle group (MDD$_{50}$) was calculated from a linear regression equation. The test results of representative compounds appear in Table V.

TABLE V

Effects on Locomotor Activity in Rats

| Compound | MDD$_{50}$ (mg/kg P.O.) |
|---|---|
| N—[3-(3-cyanopyrazolo[1,5-a]pyrimidin-7-yl)phenyl]-N—ethylpropanamide | 2.0 |
| N—[3-(3-cyanopyrazolo[1,5-a]pyrimidin-7-yl)phenyl]-N—ethylacetamide | 1.4 |

The novel compounds of the present invention have been found to be highly useful for drug therapy in mammals when administered in amounts ranging from about 0.1 mg to about 20.0 mg/kg of body weight per day. A preferred dosage regimen for optimum results would be from about 0.5 mg to about 10.0 mg/kg of body weight per day. Dosage units are employed such that a total of from about 10 to about 700 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of nonvolatile, normally liquid, polyethylene glycols which are soluble in both water and organic liquids and which have molecular weights of from about 200 to 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned nonvolatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-alpha-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05% to about 0.2% concentrations of antioxidant are employed.

For intramuscular injection, the preferred concentration of active compound is 0.25 to 0.50 mg/ml of the final compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The active compounds of the present invention may be orally administered, for example, with an inert diluent or with an assimilable edible carrier, or they may be enclosed in hard or soft shell gelatin capsules, or compressed into tablets, or incorporated directly into the food of the diet. For oral therapeutic administration, the active compounds may be incorporated with excipients and used in the form of tablets, troches, capsules, elixirs, suspensions, syrups, wafers and the like. Additionally, the active ingredient may be incorporated with the proper pharmaceutical carrier or carriers known in the art to produce a sustained-release tablet or capsule. Such compositions and preparations should contain at least 0.1% of active compound. The percentage of the compositions and preparations may, of course, be varied and may conveniently be between about 2% to about 60% of the weight of the unit dose. The amount of active compound in such therapeutically useful compositions is such that a suitable dosage will be obtained.

The tablets, troches, pills, capsules and the like may also contain one or more of the following: a binder such as gum tragacanth, acacia, corn starch or gelatin; excipients such as dicalcium phosphate; a disintegrating agent such as corn starch, potato starch, alginic acid and the like; a lubricant such as magnesium stearate; a wetting agent such as sodium lauryl sulfate and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially nontoxic in the amounts employed.

The following non-limiting examples illustrate the preparation of representative compounds of the present invention.

EXAMPLE 1

N-[3-[3-(Dimethylamino)-1-oxo-2-propenyl]phenyl]-propanamide

A 20 g portion of N-(3-acetylphenyl)propanamide in 50 ml of dimethylformamide dimethylacetal was refluxed for 8 hours, then evaporated. The residue was taken up in 200 ml of dichloromethane, passed through hydrous magnesium silicate, diluted with hexane and concentrated, giving 21.17 g of the desired compound.

Following the procedure of Example 1 and using the indicated starting materials, the amides of Examples 2-5, found in Table VI, were prepared.

TABLE VI

| Ex. | Starting Material | Amide |
|---|---|---|
| 2 | N—(3-acetylphenyl)-ethanamide | N—[3-(3-dimethylamino)-1-oxo-2-propenyl)phenyl]-acetamide |
| 3 | (3-acetylphenyl)carbamic acid, methyl ester | [3-[3-dimethylamino)-1-oxo-2-propenyl]phenyl]- |

TABLE VI-continued

| Ex. | Starting Material | Amide |
|---|---|---|
| | | carbamic acid, methyl ester |
| 4 | (3-acetylphenyl)carbamic acid, butyl ester | [3-[3-(dimethylamino)-1-oxo-2-propenyl]phenyl]-carbamic acid, butyl ester |
| 5 | N—(3-acetylphenyl)-butanamide | N—[3-[3-(dimethylamino)-1-oxo-2-propenyl]phenyl]-butanamide |

EXAMPLE 6

N-[3-[3-(Dimethylamino)-1-oxo-2-propenyl]phenyl-N-ethylpropanamide

A mixture of 3.47 g of N-[3-[3-(dimethylamino)-oxo-2-propenyl]phenyl]propanamide and 0.68 g of 60% sodium hydride in oil in dimethylformamide was stirred for 0.5 hour under argon, then cooled in an ice bath and a solution of 2.4 g of ethyl iodide in 10 ml of dimethylformamide was added in small portions. The mixture was then stirred at room temperature for 0.5 hour and extracted three times with hexane. The extracts were discarded, water was added and this mixture extracted with dichloromethane. This extract was evaporated and the residue crystallized from hexane giving the desired compound, mp 105°-107° C.

Following the procedure of Example 6 using the compounds of Examples 1-5 and appropriate alkyl halides, the alkylated amides of Examples 7-12, found in Table VII, were prepared.

TABLE VII

| Ex. | Starting Material of Ex. | Alkylated Amide | MP °C. |
|---|---|---|---|
| 7 | 2 | N—[3-[3-(dimethylamino)-1-oxo-2-propenyl]phenyl]-N—ethylacetamide | 110–113 |
| 8 | 1 | N—[3-[3-(dimethylamino)-1-oxo-2-propenyl]phenyl]-N—methylpropanamide | 148–149 |
| 9 | 2 | N—[3-[3-(dimethylamino)-1-oxo-2-propenyl]phenyl]-N—propylacetamide | 110–112 |
| 10 | 3 | [3-[3-(dimethylamino)-1-oxo-2-propenyl]phenyl]methylcarbamic acid, methyl ester | 93–95 |
| 11 | 3 | [3-[3-(dimethylamino)-1-oxo-2-propenyl]phenyl]ethylcarbamic acid, methyl ester | 95–97 |
| 12 | 2 | N—[3-[3-(dimethylamino)-1-oxo-2-propenyl]phenyl]-N—methylacetamide | 146–148 |

EXAMPLE 13

N-[3-(3-Cyanopyrazolo[1,5-a]pyrimidin-7-yl)phenyl]-N-ethylpropanamide

A mixture of 0.54 g of 3-amino-4-pyrazolecarbonitrile and 1.37 g of N-[3-[3-(dimethylamino)-1-oxo-2-propenyl]phenyl]-N-ethylpropanamide in 50 ml of glacial acetic acid was refluxed for 8 hours and then the solvent was removed. The residue was partitioned between saturated aqueous sodium bicarbonate and dichloromethane. The organic layer was separated, dried, passed through a pad of hydrous magnesium silicate and hexane was added to the refluxing filtrate. The mixture was then cooled and the solid collected, giving 1.3 g of the desired product, mp 161°-162° C.

Following the procedure of Example 13 and using appropriately substituted 3-amino-pyrazoles together with the indicated intermediates, the products of Examples 14–37 found in Table VIII were prepared.

TABLE VIII

| Ex. | Intermediate of Ex. | 3-Amino-pyrazole | Product | MP °C. |
|---|---|---|---|---|
| 14 | 7 | 3-aminopyrazole-4-carbonitrile | N—[3-(3-cyanopyrazolo[1,5-a]pyrimidin-7-yl)phenyl]-N—ethylacetamide | 186–187 |
| 15 | 7 | 3-aminopyrazole | N—ethyl-N—(3-pyrazolo[1,5-a]pyrimidin-7-ylphenyl)acetamide | 115–117 |
| 16 | 9 | 3-aminopyrazole | N—propyl-N—(3-pyrazolo[1,5-a]pyrimidin-7-ylphenyl)acetamide | 90–92 |
| 17 | 9 | 3-aminopyrazole-4-carbonitrile | N—[3-(3-cyanopyrazolo[1,5-a]pyrimidin-7-yl)phenyl]-N—propylacetamide | 151–153 |
| 18 | 6 | ethyl-3-amino-pyrazole-4-carboxylate | 7-[3-[ethyl(1-oxopropyl)amino]phenyl]pyrazolo[1,5-a]pyrimidine-3-carboxylic acid, ethyl ester | 124–126 |
| 19 | 10 | 3-aminopyrazole-4-carbonitrile | [3-(3-cyanopyrazolo[1,5-a]pyrimidin-7-yl)phenyl]methylcarbamic acid, methyl ester | 168–170 |
| 20 | 10 | ethyl-3-amino-pyrazole-4-carboxylate | 7-[3-[(methoxycarbonyl)methyl-amino]phenyl]pyrazolo[1,5-a]pyrimidine-3-carboxylic acid, ethyl ester | 115–116 |
| 21 | 3 | 3-aminopyrazole-4-carbonitrile | [3-(3-cyanopyrazolo[1,5-a]pyrimidin-7-yl)phenyl]carbamic acid, methyl ester | 256–258 |
| 22 | 4 | 3-aminopyrazole-4-carbonitrile | [3-(3-cyanopyrazolo[1,5-a]pyrimidin-7-yl)phenyl]carbamic acid, butyl ester | 131–133 |
| 23 | 1 | 3-aminopyrazole | N—[3-(pyrazolo[1,5-a]pyrimidin-7-yl)phenyl]propanamide | 177–178 |
| 24 | 1 | 3-aminopyrazole-4-carbonitrile | N—[3-(3-cyanopyrazolo[1,5-a]pyrimidin-7-yl)phenyl]propanamide | 202–204 |
| 25 | 1 | 3-amino-5-methylpyrazole-4-carbonitrile | N—[3-(3-cyano-2-methylpyrazolo[1,5-a]pyrimidin-7-yl)phenyl]propanamide | 177–178 |
| 26 | 8 | 3-aminopyrazole-4-carbonitrile | N—[3-(3-cyanopyrazolo[1,5-a]pyrimidin-7-yl)phenyl]-N—methylpropanamide | |
| 27 | 8 | 3-amino-5-methylpyrazole-4-carbonitrile | N—[3-(3-cyano-2-methylpyrazolo[1,5-a]pyrimidin-7-yl)phenyl]-N—methylpropanamide | 184–186 |
| 28 | 5 | 3-aminopyrazole-4-carbonitrile | N—[3-(3-cyanopyrazolo[1,5-a]pyrimidin-7-yl)phenyl]butanamide | 138–140 |
| 29 | 12 | 3-aminopyrazole-4-carbonitrile | N—[3-(3-cyanopyrazolo[1,5-a]pyrimidin-7-yl)phenyl]-N—methylacetamide | 195–197 |
| 30 | 2 | 3-aminopyrazole-4-carbonitrile | N—[3-(3-cyanopyrazolo[1,5-a]pyrimidine-7-yl)phenyl]acetamide | 257–259 |
| 31 | 12 | 3-aminopyrazole | N—methyl-N—(3-pyrazolo[1,5-a]pyrimidine-7-ylphenyl)acetamide | 118–120 |
| 32 | 12 | ethyl-3-amino-pyrazole-4-carboxylate | 7-[3-(acetylmethylamino)phenyl]pyrazolo[1,5-a]pyrimidine-3-carboxylic acid, ethyl ester | 155–156 |
| 33 | 7 | 3-amino-4-carbo-ethoxypyrazole | 7-[3-(acetylethylamino)phenyl]pyrazolo[1,5-a]pyrimidine-3-carboxylic acid, ethyl ester | 147–148 |
| 34 | 2 | 3-amino-4-carbo-ethoxypyrazole | 7-[3-(acetylamino)phenyl]pyrazolo[1,5-a]pyrimidine-3-carboxylic acid, ethyl ester | 202–204 |
| 35 | 3 | 3-amino-4-carbo-ethoxypyrazole | 7-[3-[(methoxycarbonyl)amino]phenyl]pyrazolo[1,5-a]pyrimidine-3-carboxylic acid, ethyl ester | 187–188 |
| 36 | 10 | 3-aminopyrazole | methyl(3-pyrazolo[1,5-a]pyrimidin-7-ylphenyl)carbamic acid, methyl ester | 107–109 |
| 37 | 9 | 3-amino-4-carbo-ethoxypyrazole | 7-[3-(acetylpropylamino)phenyl]pyrazolo[1,5-a]pyrimidine-3-carboxylic acid, ethyl ester | 156–157 |

EXAMPLE 38

N-[3-(3-Chloropyrazolo[1,5-a]pyrimidin-7-yl)phenyl]-N-ethylacetamide

A mixture of 1.0 g of N-ethyl-N-(3-pyrazolo[1,5-a]pyrimidin-7-ylphenyl)acetamide and 4.57 g of 1-chlorobenzotriazole in 50 ml of dichloromethane was refluxed for 25 minutes, then cooled and poured into 50 ml of ice-cold 2.5N aqueous sodium hydroxide. The mixture was filtered through hydrous magnesium silicate, precipitated with hexane and the solid collected, giving 0.7 g of the desired product, mp 157°–159°C.

EXAMPLE 39

7-[3-[Ethyl(methoxycarbonyl)amino]phenyl]-pyrazolo[1,5-a]pyrimidine-3-carboxylic acid, ethyl ester A 12.41 g portion of [3-[3-(dimethylamino)-1-oxo-2-propenyl]phenyl]carbamic acid, methyl ester was reacted as described in Example 6, using 9.36 g of ethyliodide, giving 13.4 g of [3-[3-(dimethylamino)-1-oxo-2-propenyl]phenyl]ethylcarbamic acid, methyl ester, mp 95°–97° C.

A 2.76 g portion of the above ester was reacted with 1.55 g of ethyl-3-aminopyrazole-4-carboxylate as described in Example 13, giving 2.87 g of the desired product, mp 117°–119 C.

EXAMPLE 40

[3-(3-Cyanopyrazolo[1,5-a]pyrimidin-7-yl)phenyl]ethylcarbamic acid, methyl ester A 2.76 g portion of [3-[3-(dimethylamino)-1-oxo-2-propenyl]phenyl]ethylcarbamic acid, methyl ester was reacted with 1.08 g of 3-aminopyrazole-4-carbonitrile as described in Example 13, giving 2.6 g of the desired product, mp 162°–164° C.

EXAMPLE 41

[3-(3-Cyanopyrazolo[1,5-a]pyrimidin-7-yl)phenyl]methylcarbamic acid, ethyl ester 1-Acetylphenyl-3-carbamic acid, ethyl ester was converted to [3-[3-(dimethylamino)-1-oxo-2-propenyl]phenyl]carbamic acid, ethyl ester by the procedure of Example 1 and this ester was then reacted with methyl iodide, again by the procedure of Example 6, giving [3-[3-(dimethylamino)-1-oxo-2-propenyl]phenyl]methylcarbamic acid, ethyl ester.

A 2.6 g portion of the above ester was reacted with 1.08 g of 3-aminopyrazole-4-carbonitrile by the procedure of Example 13, giving 2.09 g of the desired compound, mp 140°–142° C.

EXAMPLE 42

Ethyl(3-pyrazolo[1,5-a]pyrimidin-7-ylphenyl)carbamic acid, ethyl ester

[3-[3-(Dimethylamino)-1-oxo-2-propenyl]phenyl]carbamic acid was reated with ethyl iodide by the procedure of Example 6, giving [3-[3-(dimethylamino)-1-oxo-2-propenyl]phenyl]ethylcarbamic acid, ethyl ester.

A 2.9 g portion of the above ester was reacted with 0.83 g of 3-aminopyrazole by the procedure of Example 13, giving 2.27 g of the desired product, mp 79°–81° C.

EXAMPLE 43

[3-(3-Cyanopyrazolo[1,5-a]pyrimidin-7-yl)phenyl]ethylcarbamic acid, ethyl ester

A 2.0 g portion of [3-[3-(dimethylamino)-1-oxo-2-propenyl]phenyl]ethylcarbamic acid, ethyl ester was reacted with 1.08 g of 3-aminopyrazole-4-carbonitrile as described in Example 13, giving 2.52 g of the desired product, mp 133°–135° C.

EXAMPLE 44

[3-(3-Chloropyrazolo[1,5-a]pyrimidin-7-yl)phenyl]ethylcarbamic acid, ethyl ester A 1.55 g portion of ethyl(3-pyrazolo[1,5-a]-pyrimidin-7-ylphenyl)carbamic acid, ethyl ester in 50 ml of dichloromethane was reacted with 1-chlorobenzotriazole for 30 minutes, giving 1.29 g of the desired product, mp 100°–102° C.

EXAMPLE 45

N-[3-(3-Cyanopyrazolo[1,5-a]pyrimidin-7-yl)phenyl]-N-2-propenylacetamide

An 11.61 g portion of N-[3-[3-(dimethylamino)-1-oxo-2-propenyl]phenyl]acetamide was reacted with 7.26 g of allyl bromide as described in Example 6, giving 13.34 g of N-[3-[3-(dimethylamino)-1-oxo-2-propenyl]phenyl]-N-2-propenylacetamide, mp 91°–94° C.

A 1.36 g portion of the above intermediate was reacted with 0.54 g of 3-aminopyrazole-4-carbonitrile as described in Example 13, giving 1.0 g of the desired compound, mp 135°–137° C.

EXAMPLE 46

N-[3-(3-Cyanopyrazolo[1,5-a]pyrimidin-7-yl)phenyl]-N-2-propynylacetamide

An 11.61 g portion of N-[3-[3-(dimethylamino)-1-oxo-2-propenyl]phenyl]acetamide was reacted with propynyl bromide as described in Example 6, giving N-[3-[3-(dimethylamino)-1-oxo-2-propenyl]phenyl]-N-2-propynylacetamide, mp 98°–101° C.

A 2.7 g portion of the above intermediate was reacted with 1.08 g of 3-aminopyrazole-4-carbonitrile as described in Example 13, giving 1.90 g of the desired product, mp 193°–195° C.

EXAMPLE 47

N-Butyl-N-[3-(3-cyanopyrazolo[1,5-a]pyrimidin-7-yl)phenyl]acetamide

An 11.61 g portion of [3-[3-(dimethylamino)-1-oxo-2-propenyl]phenyl]carbamic acid, methyl ester was reacted with 11.0 g of butyl iodide by the procedure of Example 6, giving 16.3 g of N-butyl-N-[3-[3-(dimethylamino)-1-oxo-2-propenyl]phenyl]acetamide.

A 2.88 g portion of the above intermediate was reacted with 1.08 g of 3-aminopyrazole-4-carbonitrile by the procedure of Example 13, giving 1.61 g of the desired product, mp 146°–148° C.

EXAMPLE 48

N-[3-(3-Cyanopyrazolo[1,5-a]pyrimidin-7-yl)phenyl]-N-methylcarbamic acid, butyl ester An 11.61 g portion of [3-[3-(dimethylamino)-1-oxo-2-propenyl]phenyl]carbamic acid, butyl ester was reacted with 6.82 g of methyl iodide by the procedure of Example 6, giving 11.67 g of [3-[3-(dimethylamino)-1-oxo-2-propenyl]phenyl]methylcarbamic acid, butyl ester.

A 3.04 g portion of the above ester was reacted with 1.08 g of 3-aminopyrazole-4-carbontirile as described in Example 13, giving 2.3 g of the desired product, mp 96°–97° C.

EXAMPLE 49

N-[3-(3-Chloropyrazolo[1,5-a]pyrimidin-7-yl)phenyl]-N-methylacetamide

A 1.0 g portion of N-methyl-N-(3-pyrazolo[1,5-a]pyrimidin-7-ylphenyl)acetamide was reacted as described in Example 38, giving 1.0 g of the desired product, mp 163°–165° C.

EXAMPLE 50

[3-(3-Chloropyrazolo1,5-a]pyrimidin-7-yl)phenyl]methylcarbamic acid, methyl ester A 1.4 g portion of methyl(3-pyrazolo[1,5-a]pyrimidin-7-ylphenyl)carbamic acid, methyl ester was reacted as described in Example 38, giving 1.42 g of the desired product, mp 132°–134° C.

EXAMPLE 51

7-[3-[(Cyclopropylcarbonyl)methylamino]phenyl-pyrazolo[1,5-a]pyrimidine-3-carboxylic acid, ethyl ester N-(3-Acetylphenyl)cyclopropanecarboxamide was prepared by the reaction of m-aminoacetophenone, diisopropylethylamine and cyclopropanecarboxylic acid chloride in dichloromethane.

This compound was then converted to N-[3-[3-(dimethylamino)-1-oxo-2-propenyl]phenyl]cyclopropanecarboxamide by the procedure of Example 1 and then alkylated by the procedure of Example 6, using methyl iodide, giving 10.17 g of N-[3-(3-dimethylamino)-1-oxo-2-propenyl)phenyl]-N-methylcyclopropanecarboxamide, mp 120°–122° C.

A 0.54 g portion of this compound was reacted as described in Example 13 with 3-aminopyrazole-4-carbonitrile, giving 1.08 g of the desired product, mp 178°–180° C.

EXAMPLE 52

7-[3-[(Cyclopropylcarbonyl)methylamino]phenyl]pyrazolo[1,5-a]pyrimidine-3-carboxylic acid, ethyl ester A 0.73 g portion of ethyl 3-aminopyrazole-4-carboxylate and 1.36 g of N-[3-[(3-(dimethylamino)-1-oxo-2-propenyl]phenyl]-N-methylcyclopropanecarboxamide were reacted as described in Example 13, giving 0.52 g of the desired product, mp 122°–124° C.

EXAMPLE 53

N-[3-(3-Cyanopyrazolo[1,5-a]pyrimidin-7-yl)phenyl]-N-methylcyclobutanecarboxamide m-Aminoacetophenone, cyclobutanecarboxylic acid, chloride and diisopropylethylamine in dichloromethane were reacted, giving N-(3-acetylphenyl)cyclobutanecarboxamide.

This compound was then converted to N-[3-[3-(dimethylamino)-1-oxo-2-propenyl]phenyl]cyclobutanecarboxamide, mp 155°–157° C., by the procedure of Example 1 and further alkylated by the procedure of Example 6, using methyl iodide to give 8.32 g of N-[3-[3-(dimethylamino)1-oxo-2-propenyl]phenyl]-N-methylcyclobutanecarboxamide, mp 117°–119° C.

A 0.54 g portion of 3-aminopyrazole-4-carbonitrile was reacted with 1.43 g of the above product by the procedure of Example 13, giving 1.3 g of the desired product, mp 157°–158° C.

EXAMPLE 54

7-[3-[(Cyclobutylcarbonyl)amino]phenyl]pyrazolo[1,5-a]pyrimidine-3-carboxylic acid, ethyl ester A 0.78 g portion of 3-amino-4-carboethoxypyrazole ard 1.36 g of N-[3-[3-(dimethylamino)-1-oxo-2-propenyl]phenyl]cyclobutanecarboxamide were reacted as described in Example 13, giving 1.52 g of the desired product, mp 123°–125° C.

What is claimed is:

1. A compound of the formula:

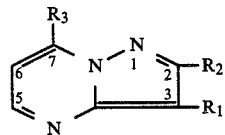

wherein $R_1$ is selected from the group consisting of hydrogen, halogen, cyano and

$R_2$ is selected from the group consisting of hydrogen and alkyl ($C_1$–$C_3$); $R_3$ is

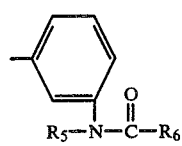

$R_4$ is selected from the group consisting of hydrogen, alkyl($C_1$–$C_6$) and alkoxy($C_1$–$C_6$); $R_5$ is selected from the group consisting of hydrogen, alkyl($C_1$–$C_6$), alkenyl($C_2$–$C_6$), —CH$_2$C≡CH, cycloalkyl($C_3$–$C_6$)methyl, —CH$_2$OCH$_3$ and —CH$_2$CH$_2$OCH$_3$; and $R_6$ is selected from the group consisting of alkyl($C_1$–$C_6$), cycloalkyl($C_3$–$C_6$), —O-alkyl($C_1$–$C_6$), —NH-alkyl($C_1$–$C_3$), —N-dialkyl($C_1$–$C_3$), —(CH$_2$)$_n$—O-alkyl($C_1$–$C_3$), —(CH$_2$)$_n$—NH-alkyl($C_1$–$C_3$) and —(CH$_2$)$_n$—N-dialkyl($C_1$–$C_3$), where n is an integer 1 to 3 inclusive.

2. A compound according to claim 1, wherein $R_1$ is cyano or

$R_2$ is hydrogen; $R_4$ is alkyl($C_1$–$C_6$), alkenyl($C_2$–$C_6$) or —CH$_2$≡CH; and $R_6$ is alkyl ($C_1$–$C_6$), cycloalkyl($C_3$–$C_6$) or —O-alkyl($C_1$–$C_6$).

3. The compound according to claim 2, which is N-[3-(3-cyanopyrazolo[1,5-a]pyrimidin-7-yl)phenyl]-N-ethylpropanamide.

4. The compound according to claim 2, which is N-[3-(3-cyanopyrazolo[1,5-a]pyrimidin-7-yl)phenyl]-N-ethylacetamide.

5. The compound according to claim 2, which is N-[3-(3-cyanopyrazolo[1,5-a]pyrimidin-7-yl)phenyl]-N-propylacetamide.

6. The compound according to claim 2, which is [3-(3-cyanopyrazolo[1,5-a]pyrimidin-7-yl)phenyl]methylcarbamic acid, methyl ester.

7. The compound according to claim 2, which is 7-[3-[(methoxycarbonyl)methylamino]phenyl]pyrazolo[1,5-a]pyrimidine-3-carboxylic acid, ethyl ester.

8. The compound according to claim 2, which is [3-(3-cyanopyrazolo[1,5-a]pyrimidin-7-yl)phenyl]ethylcarbamic acid, methyl ester.

9. The compound according to claim 2, which is ethyl(3-pyrazolo[1,5-a]pyrimidin-7-ylphenyl)carbamic acid, ethyl ester.

10. The compound according to claim 2, which is [3-(3-chloropyrazolo[1,5-a]pyrimidin-7-yl)phenyl]ethylcarbamic acid, ethyl ester.

11. The compound according to claim 2, which is N-[3-(3-cyanopyrazolo[1,5-a]pyrimidin-7-yl)phenyl]-N-2-propenylacetamide.

12. The compound according to claim 2, which is N-[3-(3-cyanopyrazolo[1,5-a]pyrimidin-7-yl)phenyl]-N-2-propynylacetamide.

13. The compound according to claim 2, which is N-[3-(3-cyanopyrazolo[1,5-a]pyrimidin-7-yl)phenyl]-N-methylacetamide.

14. A method of ameliorating anxiety in a mammal which comprises administering to said mammal an amount of a compound of claim 1 sufficient to reduce anxiety.

15. A composition of matter in dosage unit form comprising from 2–750 mg of a compound of claim 1 in association with a pharmaceutically acceptable carrier.

* * * * *

UNITED STATES PATENT AND TRADEMARK OFFICE
CERTIFICATE OF CORRECTION

PATENT : 4,626,538
DATED : December 2, 1986
INVENTOR(S) : Dusza et al

It is certified that error appears in the above-identified patent and that said Letters Patent is hereby corrected as shown below:

On the title page, the "[*] Notice" should read as follows:

--[*] Notice: This patent is subject to a terminal disclaimer.--.

Signed and Sealed this

Ninth Day of May, 2000

Attest:

Q. TODD DICKINSON

*Attesting Officer*   *Director of Patents and Trademarks*